United States Patent [19]

Sakamoto et al.

[11] 4,188,955
[45] Feb. 19, 1980

[54] BLOOD PRESSURE MEASURING PROCESS AND APPARATUS

[75] Inventors: Tamaki Sakamoto, Nagaokakyo; Yoshio Kinefuchi, Takatsuki, both of Japan

[73] Assignee: Omron Tateisi Electronics Co., Kyoto, Japan

[21] Appl. No.: 832,475

[22] Filed: Sep. 12, 1977

[51] Int. Cl.² .............................................. A61B 5/02
[52] U.S. Cl. .................................................... 128/680
[58] Field of Search .................. 128/2.05 A, 2.05 M, 128/2.05 Q, 680

[56] References Cited
U.S. PATENT DOCUMENTS

| | | | |
|---|---|---|---|
| 3,137,292 | 6/1964 | Richter et al. | 128/2.05 A |
| 3,654,915 | 4/1972 | Sanctuary | 128/2.05 M |
| 3,814,083 | 6/1974 | Fletcher et al. | 128/2.05 A |
| 3,905,354 | 9/1975 | Lichowsky | 128/2.05 M |
| 3,978,848 | 9/1976 | Yen et al. | 128/2.05 M |
| 4,027,662 | 6/1977 | Lee | 128/2.05 A |
| 4,033,336 | 7/1977 | Murawski et al. | 128/2.05 R |
| 4,058,117 | 11/1977 | Kaspari et al. | 128/2.05 A |
| 4,116,230 | 9/1978 | Gorelick | 128/2.05 M |

FOREIGN PATENT DOCUMENTS 49-35793 9/1974 Japan .................................. 128/2.05 A Primary Examiner—Robert W. Michell
Assistant Examiner—Francis J. Jaworski
Attorney, Agent, or Firm—Stevens, Davis, Miller & Mosher

[57] ABSTRACT

A process and apparatus for automatically measuring blood pressure, particularly diastolic pressure, in a shortened period of time. A first predetermined pressure range below a determined systolic level is established and, if Korotkov pulse sounds are received as cuff pressure decreases through this range, a cuff pressure corresponding to a last detected Korotkov sound is determined as a diastolic pressure when no Korotkov pulse sounds are received in a third narrow pressure range beginning at the cuff pressure coresponding to the last detected Korotkov sound. If Korotkov sounds disappear during decrease of cuff pressure through the first pressure range a cuff pressure corresponding to a last detected Korotkov sound is determined as a diastolic pressure when no Korotkov sounds are received in a second wide predetermined pressure range beginning at the cuff pressure corresponding to the last detected Korotkov sound.

7 Claims, 4 Drawing Figures

BLOOD PRESSURE MEASURING PROCESS AND APPARATUS

BACKGROUND OF THE INVENTION

This invention relates to a blood pressure measuring process and apparatus for automatically measuring systolic and diastolic blood pressures.

As is well known, typical conventional measurement of blood pressure is obtained by the use of an inflatable cuff which is wrapped around the arm of a patient or person. The cuff is inflated to occlude blood flow, then the pressure in the cuff is gradually decreased. At the instant a first acoustic pulse, called a Korotkov sound, is detected, the cuff pressure represents the systolic blood pressure. The pressure in the cuff is further decreased until the acoustic pulses disappear. At this point, another pressure reading is taken which serves as the diastolic blood pressure. However, it is often the case that the Korotkov sounds disappear even though the cuff pressure is higher than the true diastolic blood pressure, and they again appear when the pressure in the cuff is futher decreased, as shown in FIG. 1. The interval of disappearance of the Korotkov sounds, which is typical of some patients, is called the auscultatory gap. By the reason of the above, accurate measurments of diastolic blood pressure of some patients are not always obtained by detecting for the disappearance of Korotkov sounds.

A proposed measuring apparatus for accurately and automatically measuring diastolic blood pressure of patients having an auscultatory gap is shown in the published specification No. 35798/1974 of a Japanese patent application. This reference discloses a blood pressure measurement which is discontinued if Korotkov sounds are not detected within a predetermined time period of about 7 seconds, which corresponds to a pressure decrease of 20 mmHg after the Korotkov sounds disappear. Since the measurement shown in this reference always requires a time period of 7 seconds after the detection of the last Korotkov sounds, it is disliked by patients whether or not they have an auscultatory gap Further, inaccurate measurement is often unavoidable since the rate of pressure decrease often varies, causing a variation in the predetermined time period.

SUMMARY OF THE INVENTION

Thus, it is an object of the present invention to provide a process and apparatus for measuring the blood pressure of an individual which provides an accurate measurement of systolic and diastolic blood pressure in a short time.

The present invention is based on the discovery that the auscultatory gap almost always appears before the pressure in the cuff decreases by about 15 mmHg after the first detection of the Korotkov sound.

In accordance with the present invention, when Korotkov sounds disappear before the pressure in the cuff decreases by a predetermined first reference range of 13–20 mmHg, for example, 15 mmHg, from the first detection of the Korotkov sound, the measurement is continued until the pressure in the cuff further decreases by a predetermined second reference range of 15–25 mmHg, for example, 20 mmHg, and when Korotkov sounds appear after the pressure decreases in the predetermined first reference range of 15 mmHg from the first detection of the Korotkov sound, the measurement is further continued unless the Korotkov sound disappears during a predetermined third reference range of pressure decrease of 4–8 mmHg, for example, 6 mmHg.

DETAILED DESCRIPTION OF THE INVENTION

Figure 2:
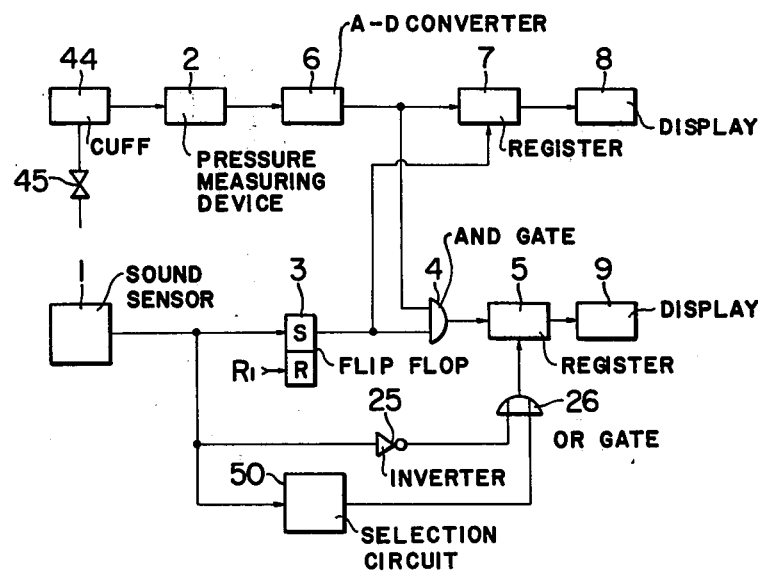
FIG. 2 is a block diagram of the blood pressure measuring apparatus of the present invention.

Referring first to FIG. 2, an inflatable cuff 44 is wrapped around the arm of a patient or person and is inflated by means of pressurized air supply to a pressure occluding blood flow, then the pressure is substantially linearly decreased through an exhausting valve 45 at a rate of, for example, 2–3 mmHg/sec. A Korotkov sound sensor 1 is attached to an interior surface of the cuff 44 so that the sensor 1 is placed over an artery of a patient's arm. The Korotkov sound sensor 1 comprises a microphone and noise limiting circuit. When the pressure in the cuff is high enough to occlude blood flow, no Korotkov sound is generated; while when the pressure in the cuff is decreased to a certain level, Korotkov sounds can be generated. The pressure in the cuff 44 is measured by a pressure measuring device 2 having an electrical output which is fed to an analog-digital converter 6. A digital signal from the A-D converter 6 is fed to a register 7 and is displayed by a visual display 8. At the instant the first Korotkov sound is detected, the digital signal of the pressure or the systolic blood pressure signal is retained by the register 7 which is inhibited by the output of a flip-flop 3 from reading another signal thereafter so that the display of the systolic blood pressure at the display 8 remains.

A diastolic blood pressure is measured and displayed as described below. An AND gate 4 is opened by the output of the flip-flop circuit 3 when the sensor 1 detects a Korotkov sound as described above, and the pressure signals from the A-D converter 6 which represent a possible diastolic pressure are fed to a register 5 through the AND gate 4 under control of inverter 25. The possible diastolic blood pressure signal, is verified as a true diastolic pressure and the register 5 is inhibited from storing further data by a selecting circuit 50 as described below. The diastolic blood pressure signal retained by the register 5 is fed to the display 9, where it is continuously displayed.

Figure 3:
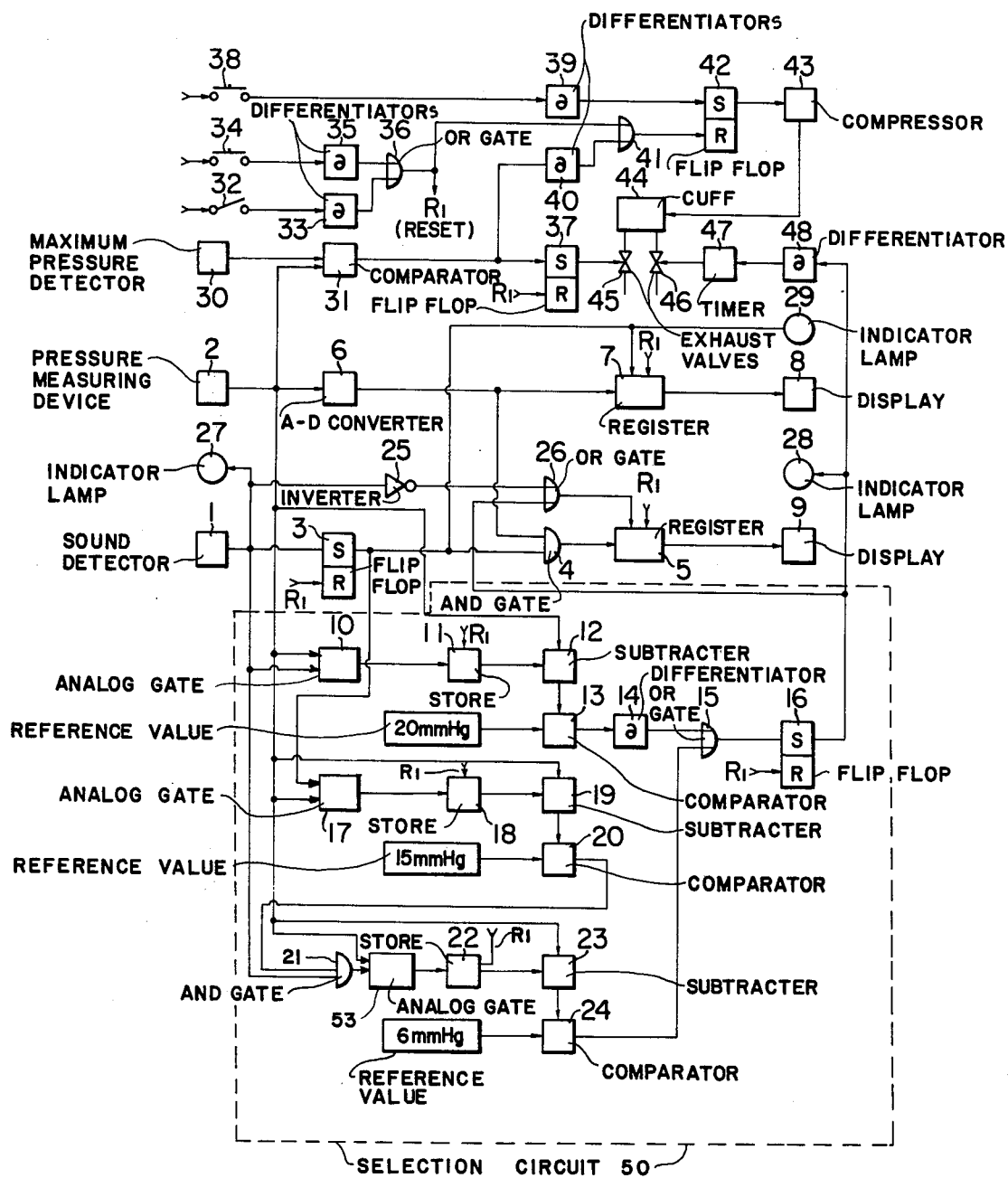
FIG. 3 is a detailed block diagram of one embodiment of the present invention.

Referring now to FIG. 3, when the first Korotkov sound is detected by the sensor 1, the output of the flip-flop circuit 3 is fed to register 7 enabling it to store a systolic pressure level signal from A-D converter 6. The flip-flop 3 output is also fed to an analog gate 17 to enable the output of the pressure measuring device 2 to be fed to a maximum analog value retaining circuit 18. Since the pressure in the cuff is gradually decreased, the retaining circuit 18 retains a maximum pressure signal constituting a function of the systolic blood pressure. Electrical signals representing the maximum pressure and the continuously decreasing cuff pressure are fed to a subtraction circuit 19 where the decreasing pressure is subtracted from the maximum pressure. The output of the subtraction circuit 19 and a predetermined first reference voltage signal which represents a pressure range of, for example, 15 mmHg, are fed to a comparator 20 where they are compared. When the pressure in the cuff decreases 15 mmHg below the maximum pressure, the comparater 20 provides an output which is fed to an AND gate 21 which further receives outputs of the sensor 1 and the pressure measuring device 2.

Since the Korotkov sounds appear with pulse sounds, the output of the pressure measuring device 2 is intermittently fed via gate 53 to a retaining circuit 22 under control of AND gate 21. The outputs of the retaining circuit 22 and the pressure measuring device 2 are fed to a subtraction circuit 23 where they are subtracted. The output of the subtraction circuit 23 and a predetermined third reference voltage signal which represents a pressure range of, for example, 6 mmHg, are fed to a comparator 24 and compared. The predetermined value of 6 mmHg is selected to be slightly higher than the amount of pressure decrease which occurs during an interval of one cycle of pulse sounds.

Figure 1:
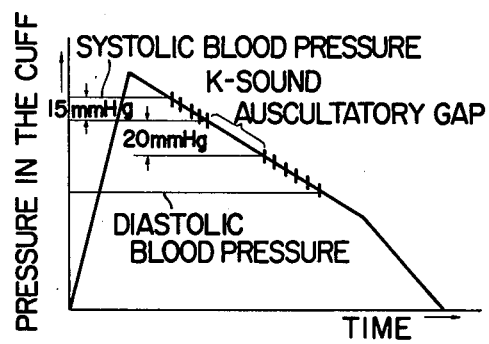
FIG. 1 is a graph showing the wave form of the pressure in the cuff.

Referring to FIG. 1 and FIG. 3, after the pressure in the cuff decreases 15 mmHg below the systolic blood pressure, the output of the comparator 20 enables the analog gate 53 under control of AND gate 21 to pass pressure signals from the pressure measuring device 2 to the retaining circuit 22 at every Korotkov sound.

The output of the subtraction circuit 23 shows the pressure decrease of an interval of one cycle of pulse sounds. At first, the output of the subtraction circuit 23 indicates a pressure drop of less than 6 mmHg since Korotkov sounds are continuously generated. After the diastolic blood pressure appears, no Korotkov sound is detected, thus the output of the subtracting circuit 23 indicates a pressure decrease greater than 6 mmHg, and the output of the comparator 24 which is a signal verifying the detection of a diastolic pressure is generated.

The diastolic pressure verification signal sets a flip-flop circuit 16 through OR gate 15, the output of which inhibits the register 5 from reading another signal through an OR gate 26. Since the register 5 is inhibited from reading another signal by the output of an inverter 25, after the last detected Korotkov sound, the output of register 5 indicates the diastolic blood pressure which is thereafter displayed at the visual display 9.

As described above, the first reference signal sets the first range excluding initiation of the auscultatory gap, the third reference signal sets the third range for continuing the measurement unless the Korotkov sound disappears in the third range.

A retaining circuit 11 retains the signal of pressure in the cuff which is fed through an analog gate 10 at every Korotkov sound signal. The pressure signal from 2 which varies at every second and the retained signal are fed to a subtraction circuit 12 and are subtracted.

The output of the subtraction circuit 12 is compared with a predetermined second reference voltage signal which represents a range of pressure decrease of, for example, 20 mmHg, or an auscultatory gap.

Figure 4:
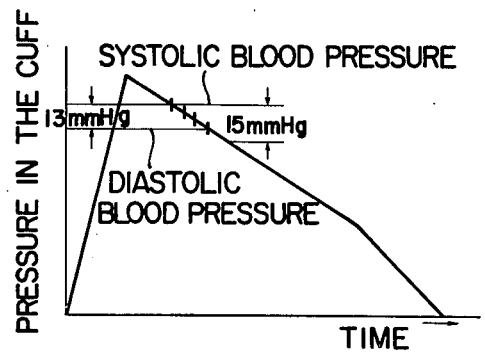
FIG. 4 is a graph showing another wave form of the pressure in the cuff.

The output of the comparator 13 is not generated when Korotkov sounds intermittently appear. However, if no Korotkov sounds appear during a pressure decrease of 20 mmHg below the pressure at which the last Korotkov sound appeared, the comparator 13 generates an output indicating that the pressure at the last Korotkov sound is the diastolic pressure. The output of the comparator 13 is the diastolic blood pressure verification signal. It is fed to the flip-flop circuit 16 through the OR gate 15 after being differentiated by the differentiator 14. When the difference between the systolic and diastolic blood pressure is within 15 mmHg, as shown in FIG. 4, no Korotkov sound is generated after the pressure decrease of 15 mmHg from the systolic blood pressure, consequently the AND gate 21 cannot be opened. As a result, no verification signal of the diastolic blood pressure is fed to the flip-flop circuit 16. In such a case, the comparator 13 feeds a signal to the flip-flop circuit 16, causing the diastolic blood pressure to be displayed. If the Korotkov sound appears again before a further pressure decrease of 20 mmHg, and AND gate 21 is opened.

An indicating lamp 27 is actuated by every signal from the Korotkov sound sensor 1.

An indicating lamp 29 for indicating systolic blood pressure is actuated by the output of the flip-flop circuit 3, and an indicating lamp 28 for indicating diastolic blood pressure is actuated by the output of the flip-flop circuit 16.

The indication at the visual display 8 varies with the pressure decrease until the systolic blood pressure is detected. Once the systolic blood pressure is detected, the indication at the display 8 is fixed, at the same time the lamp 29 is turned on, thus the indication of the systolic blood pressure remains thereafter.

The indication at the display 9 varies with every Korotkov sound detection until the diastolic blood pressure is detected. Once the systolic blood pressure is detected, the indication at the display 9 is fixed, at the same time the lamp 28 is turned on, thus the indication of the diastolic blood pressure remains thereafter. The lamp 28 indicates the conclusion of blood pressure measurement.

To start the measurement of blood pressure using an apparatus of the present invention, first, a power switch 32 is closed. With the switch on, a differentiated signal from a differentiator 33 resets registers 5, 7, retaining circuit 11, and flip-flop circuit 3, 16, 37, 42. With closing of a switch 38, the flip-flop circuit 42 is set, the output of which switches on a compressor 43 for supplying compressed air to the cuff 44. As described above, pressure in the cuff 44 is measured by the pressure measuring device 2, the output of which and a signal from an adjusting means 30 for predetermining a maximum pressure are fed to comparator 31 and are compared. At the instant the pressure reaches the predetermined pressure, the output of the comparator 31 resets the flip-flop 42, turning off the compressor. Also, the output of the comparator 31 sets a flip-flop circuit 37, the output of which causes the opening of an exhausting valve 45 to decrease pressure in the cuff 44 at a predetermined rate of, for example, 2-3 mmHg/sec. After the diastolic blood pressure is detected, the pressure in the cuff 44 is rapidly decreased through a rapid exhausting valve 46 which is opened by the output of the flip-flop 16 through a differentiator 48 and a timer 47. If the power switch 32 remains turned on, a repeated measurement is started by turning on a reset switch 34 and a switch 38.

What is claimed is:

1. A blood pressure measuring apparatus comprising:
   an inflatable cuff;
   means for pressurizing said cuff to a predeterming pressure level;
   means attached to said cuff for detecting Korotkov sounds;
   means for gradually deflating said cuff from said predetermined pressure level;

means for measuring pressure in said cuff;

systolic pressure detecting means connected with said means for measuring and said means for detecting and responsive to a first detected Korotkov sound signal occurring during cuff deflation for storing a cuff pressure existing at the time of said first Korotkov sound signal as a systolic pressure signal;

diastolic pressure detecting means connected with said means for measuring and means for detecting and responsive to a last detected Korotkov sound signal occurring during cuff deflation for storing a cuff pressure existing at the time of said last detected Korotkov sound signal as a diastolic pressure signal, said diastolic pressure detecting means comprising:

means initiated upon detection of a systolic pressure level for storing the cuff pressure existing at the time of a detected Korotkov sound as a possible true diastolic pressure level;

means responsive to the continued detection of Korotkov sounds as the cuff pressure falls through a first predetermined pressure range beginning at the systolic pressure level and thereafter to the disappearance of Korotkov sounds as the cuff pressure falls through a third predetermined pressure range beginning at the cuff pressure existing at a last detected Korotkov sound for verifying that the stored cuff pressure existing at a last detected Korotkov sound is a true diastolic pressure; and means responsive to the disappearance of Korotkov sounds as the cuff pressure falls through said first predetermined pressure range and thereafter to the disappearance of Korotkov sounds as the cuff pressure falls through a second predetermined pressure range for verifying that the stored cuff pressure existing at a last detected Korotkov sound is a true diastolic pressure.

2. A blood pressure measuring apparatus as in claim 1 wherein said third predetermined pressure range is narrower than said first and second predetermined pressure ranges.

3. A blood pressure measuring apparatus as in claim 2 wherein said second predetermined pressure range is wider than said first predetermined pressure range.

4. A blood pressure measuring apparatus as in claim 3 wherein said first range is approximately 15 mmHg, said second range is approximately 20 mmHg and said third range is approximately 6 mmHg.

5. A blood pressure measuring apparatus comprising:
an inflatable cuff;
means for pressurizing said cuff to a predetermined pressure level;
means attached to said cuff for detecting Korotkov sounds;
means for gradually deflating said cuff from said predetermined pressure level;
means for measuring pressure in said cuff;
systolic pressure detecting means connected with said means for measuring and said means for detecting and responsive a first detected Korotkov sound signal occurring during cuff deflation for storing a cuff pressure existing at the time of said first Korotkov sound signal as a systolic pressure signal;
diastolic pressure detecting means connected with said means for measuring and means for detecting and responsive to a last detected Korotkov sound signal occurring during cuff deflation for storing a cuff pressure existing at the time of said last Korotkov sound signal as a diastolic pressure signal, said diastolic pressure detecting means comprising:

means initiated upon detection of a systolic pressure level for storing the cuff pressure existing at the time of a detected Korotkov sound as a possible true diastolic pressure level; and means for determining whether a stored cuff pressure is a true diastolic pressure, said means for determining comprising:

means initiated upon detection of a systolic pressure for storing said systolic pressure as a first signal;

means for subtracting a decreasing cuff pressure signal from said first signal to provide a second signal;

means for comparing said second signal with a first predetermined reference value corresponding to a first predetermined pressure range and for providing a third signal when said second signal reaches said first reference value;

means responsive to the coincident presence of said third signal and a detected Korotkov sound for storing a cuff pressure existing at the time of said detected Korotkov sound as a fourth signal;

means for subtracting a decreasing cuff pressure signal from said fourth signal to provide a fifth signal;

means for comparing said fifth signal with a second predetermined reference value corresponding to a second predetermined pressure range and for providing a sixth signal when said fifth signal reaches said second predetermined value;

means responsive to detected Korotkov sounds for storing a cuff pressure existing at the time of a detected Korotkov sound as a seventh signal;

means for subtracting a decreasing cuff pressure signal from said seventh signal to provide an eighth signal;

means for comparing said eighth signal with a third predetermined threshold value corresponding to a third predetermined reference range and for providing a ninth signal when said eighth signal reaches said third threshold value; and means responsive to the presence of said sixth or ninth signals for determining that a stored possible diastolic pressure level is a true diastolic pressure level.

6. A process for measuring blood pressure comprising the steps of:
inflating a blood pressure cuff to occlude blood flow;
gradually decreasing the pressure in said cuff;
detecting the first Korotkov sound emitted from a Korotkov detector associated with said cuff and establishing the cuff pressure existing at the time of detection of said first Korotkov sound as a systolic pressure level;
detecting for the disappearance of Korotkov sounds during a decrease of cuff pressure through a first pressure range beginning at said systolic pressure level; when Korotkov sounds are detected during a decrease of cuff pressure through said first predetermined pressure range, thereafter establishing the cuff pressure existing at the time of a last detected Korotkov pulse as a diastolic pressure when Korotkov sounds are not detected in a third pressure range beginning at the cuff pressure existing at the time of a last detected Korotkov sound, when Korotkov sounds are not detected during said first predetermined pressure range thereafter establishing the cuff pressure existing at the time of a last detected Korotkov pulse as a diastolic pressure when Korotkov sounds are not detected in a second pressure range beginning at the cuff pressure existing at the time of a last detected Korotkov sound.

7. A process as in claim 6 wherein said first predetermined pressure range is approximately 15 mmHg, said second predetermined pressure range is approximately 20 mmHg and said third pressure range is approximately 6 mmHg.

* * * * *